(12) United States Patent
Chung et al.

(10) Patent No.: US 11,926,860 B2
(45) Date of Patent: Mar. 12, 2024

(54) METHOD OF SCREENING INHIBITOR OF CASPASE ACTIVITY BY LIPOPOLYSACCHARIDE

(71) Applicant: KOREA INSTITUTE OF SCIENCE AND TECHNOLOGY, Seoul (KR)

(72) Inventors: Hak Suk Chung, Seoul (KR); Jinsu An, Seoul (KR); Eun Gyeong Yang, Seoul (KR); So Yeon Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 37 days.

(21) Appl. No.: 17/485,606

(22) Filed: Sep. 27, 2021

(65) Prior Publication Data
US 2022/0220529 A1    Jul. 14, 2022

(30) Foreign Application Priority Data
Jan. 14, 2021    (KR) ......................... 10-2021-0005223

(51) Int. Cl.
*C12Q 1/02*        (2006.01)
*C12N 9/64*        (2006.01)
*G01N 33/58*       (2006.01)

(52) U.S. Cl.
CPC .......... *C12Q 1/025* (2013.01); *C12N 9/6472* (2013.01); *C12Y 304/22057* (2013.01); *C12Q 2527/127* (2013.01); *C12Y 304/22036* (2013.01); *C12Y 304/22055* (2013.01); *C12Y 304/22056* (2013.01); *C12Y 304/22062* (2013.01); *C12Y 304/22064* (2013.01); *G01N 33/582* (2013.01); *G01N 2400/50* (2013.01); *G01N 2500/00* (2013.01)

(58) Field of Classification Search
CPC .... C12Y 304/22036; C12Y 304/22055; C12Y 304/22056; C12Y 304/22062; C12Y 304/22064; C12Y 304/22057; C12Q 1/025; C12Q 2527/127; C12N 9/6472; G01N 2500/00; G01N 33/582; G01N 2400/50
USPC ....................................................... 435/183
See application file for complete search history.

(56) References Cited

FOREIGN PATENT DOCUMENTS

JP    2012-159356 A    8/2012

OTHER PUBLICATIONS

Hiscott et al [Trends in Molecular Medicine: MasterCARD: a priceless link to innate immunity; vol. 12 No. 2 pp. 53-56] (Year: 2006).*
Shalini et al [Cell Death and Differentiation: Old, new and emerging functions of caspases: vol. 22, pp. 526-539] (Year: 2015).*
Snapp [Current Protocols in Cell Biology: Design and Use of Fluorescent Fusion Proteins in Cell Biology: vol. 27, Issue 1 Unit 21, pp. 1-17 (Year: 2005).*
Lu et al [Cell: Unified Polymerization Mechanism for the Assembly of ASC-Dependent Inflammasomes: vol. 156 pp. 1193-1206 (Year: 2014).*
Shi et al [Nature: Inflammatory caspases are innate immune receptors for intracellular LPS: vol. 514, pp. 187-204] Cited on IDS filed on Nov. 23, 2022 (Year: 2014).*
Rathinam et al., "Innate immunity to intracellular LPS", Nat Immunol., May 2019, vol. 20, No. 5, pp. 527-533, HHS Public Access Author manuscript, total 17 pages.
Smith et al., "Caspases come together over LPS", Trends Immunol., Feb. 2015, vol. 36, No. 2, pp. 59-61, NIH-PA Author Manuscript, total 4 pages.
Wong et al., "A lipopolysaccharide binding heteromultivalent dendrimer nanoplatform for Gram negative cell targeting", Journal of Materials Chemistry B, 2015, vol. 3, pp. 1149-1156.
Yang et al., "Non-canonical activation of inflammatory caspases by cytosolic LPS in innate immunity", Current Opinion in Immunology, 2015, vol. 32, pp. 78-83.
Office Action dated Aug. 29, 2022, in Korean Patent Application No. 10-2021-0005223.
Shi et al., "Inflammatory caspases are innate immune receptors for intracellular LPS," Nature (Oct. 9, 2014), vol. 514, pp. 187-192.

* cited by examiner

*Primary Examiner* — Richard G Hutson
(74) *Attorney, Agent, or Firm* — Birch, Stewart, Kolasch & Birch, LLP

(57) ABSTRACT

Provided are a method of screening an inhibitor of caspase activity by lipopolysaccharide and a method of screening a therapeutic agent for inflammatory diseases or sepsis using the same. Accordingly, it is possible to develop a caspase-4-specific inhibitor.

7 Claims, 21 Drawing Sheets
Specification includes a Sequence Listing.

METHOD OF SCREENING INHIBITOR OF CASPASE ACTIVITY BY LIPOPOLYSACCHARIDE

CROSS-REFERENCE TO RELATED APPLICATION

This application is based on and claims priority under 35 U.S.C. § 119 to Korean Patent Application No. 10-2021-0005223, filed on Jan. 14, 2021, in the Korean Intellectual Property Office, the disclosure of which is incorporated by reference herein in its entirety.

BACKGROUND

1. Field

The present disclosure relates to a method of screening an inhibitor of caspase activity by lipopolysaccharide and a method of screening a therapeutic agent for inflammatory diseases or sepsis using the same.

2. Description of the Related Art

Lipopolysaccharide (LPS) is a component of the outer membrane surrounding peptidoglycan in Gram-negative bacteria. LPS consists of lipid A and various types of sugars covalently bound thereto, and among the components of LPS, lipid A is known as an endotoxin responsible for the toxicity of Gram-negative bacteria. When a host is exposed to excessive amounts of LPS, it may cause inflammation, and in severe cases, sepsis.

Caspase is a cysteine-aspartic protease or a cysteine-dependent aspartate-directed protease, which is a proteolytic enzyme that plays an essential role in apoptosis, necrosis, inflammation, etc. Caspase activation and recruitment domain (CARD) is an interaction motif identified in several types of proteins, and is mainly involved in inflammation and apoptosis. It is known that CARD from caspase-4, caspase-5, or caspase-11 recognizes LPS, which is an endotoxin that is a main cause of sepsis, and activates caspase-4, caspase-5, or caspase-11 to cause pyroptosis through formation of inflammasomes and non-canonical inflammasomes, leading to septic shock or sepsis. Mouse caspase-11, which is a homolog of human caspase-4 and caspase-5, is known to play an important role in various inflammatory diseases, such as inflammatory bowel disease, multiple sclerosis, amyotrophic lateral sclerosis, Parkinson's disease, aging, and rheumatoid arthritis. Therefore, caspase-4 may be a promising therapeutic target for treating these diseases.

Several inhibitors, such as Z-VAD-FMK targeting an active site of caspase-4, have been reported. However, these inhibitors have also been reported to inhibit other caspases. Since several caspases have the same substrate, it may be difficult to develop caspase-4-specific inhibitors targeting the active site.

Accordingly, to develop caspase-4-specific inhibitors, it is necessary to develop a method of screening inhibitors capable of inhibiting the binding of caspase-4 and LPS.

SUMMARY

Provided is a method of screening an inhibitor of caspase activity by lipopolysaccharide (LPS).

Provided is a method of screening an inhibitor of caspase activity by LPS as a therapeutic agent for inflammatory diseases or sepsis.

Provided is a method of monitoring a therapeutic agent for inflammatory diseases or sepsis.

Provided is a composition for screening for an inhibitor of caspase activity by LPS.

Additional aspects will be set forth in part in the description which follows and, in part, will be apparent from the description, or may be learned by practice of the presented embodiments of the disclosure.

An aspect provides a method of screening for an inhibitor of caspase activity by lipopolysaccharide (LPS), the method including incubating a mixture including a polypeptide, lipopolysaccharide (LPS), and a test material, the polypeptide including a caspase activation and recruitment domain (CARD) labeled with a fluorescent material; measuring a fluorescence polarization (FP) value of the mixture; and selecting the test material as an inhibitor of binding of CARD and LPS, when the measured FP value is lowered, as compared with that of a negative control not treated with the test material.

The method includes incubating a mixture including a polypeptide, LPS, and a test material, the polypeptide including CARD labeled with a fluorescent material.

The LPS is one of the components of the outer membrane surrounding peptidoglycan in Gram-negative bacteria. LPS consists of lipid A and various types of sugars covalently bound thereto, and among the components of LPS, lipid A is known as an endotoxin responsible for the toxicity of Gram-negative bacteria. LPS may be Ra-LPS, Rb-LPS, Rc-LPS, Rd1-LPS, Rd2-LPS, or Re-LPS depending on the type of sugar. The LPS may be bound to an antigen such as an O-antigen.

The term "caspase" refers to a cysteine-aspartic protease or cysteine-dependent aspartate-directed protease, which is a proteolytic enzyme that plays a role in apoptosis, necrosis, and inflammation. The caspase is composed of a CARD domain, a large subunit, and a small subunit. The caspase may be expressed as an inactive caspase precursor in cells. The caspase precursor may form active caspase by autolysis inside cells. The active caspase may include a large subunit of about 17 kDa and a small subunit of about 12 kDa or about 10 kDa.

The caspase may be selected from the group consisting of caspase-1, caspase-2, caspase-4, caspase-5, caspase-9, caspase-11, caspase-12, caspase-13, and caspase-14, and may be specifically caspase-4, caspase-5, or caspase-11. The caspase-4 is a protease that cleaves other proteins at an aspartic acid residue. The caspase-4 is a human-derived protein, and a mouse homolog to caspase-4 is caspase-11.

The caspase may be a wild-type caspase or a mutant caspase. The mutant caspase may be a caspase (C258A), in which cysteine (C), which is a $258^{th}$ amino acid from its N-terminus, is substituted with alanine (A). The caspase may be a protein including an amino acid sequence selected from the group consisting of SEQ ID NOS: 1, 7, 9, and 13. The caspase may include an amino acid sequence encoded by a nucleotide sequence selected from the group consisting of SEQ ID NOS: 2, 8, 10, and 14.

The inhibitor of caspase activity or the inhibitor of caspase activity by LPS may be an inhibitor that inhibits binding of CARD of the caspase and LPS.

The CARD, which is an LPS-binding domain, may be a CARD variant having cysteine (Cys) inserted therein. The CARD variant may have cysteine inserted at the N-terminus of the CARD; at the C-terminus of a peptide tag and the N-terminus of the CARD; or at the C-terminus of the CARD, and specifically, may have cysteine inserted at the N-terminus or C-terminus of the CARD, for example, may have cysteine inserted at the C-terminus of the peptide tag and at the N-terminus of the CARD. The peptide tag may be a polyhistidine tag (e.g., 6×His), FLAG, GST, MBP, NusA, thioredoxin, ubiquitin, BAP, STREP, CBP, CBD, hemagglutinin (HA), S-tag, or a combination thereof. The fluorescent material may be conjugated through cysteine. The fluorescent material may be conjugated to a thiol group of cysteine.

The fluorescent material may be selected from the group consisting of ALEXA FLUOR 488, ALEXA FLUOR 425, ALEXA FLUOR 532, ALEXA FLUOR 550, TEXAS RED, ALEXA FLUOR 590, ALEXA FLUOR 647N, ALEXA FLUOR 655, BODIPY, fluorescein, and rhodamine.

The test material refers to a candidate material to be screened.

The mixture may not include bovine serum albumin (BSA), a surfactant, a divalent cation, or a combination thereof. The surfactant may be NP-40. The divalent cation may be a magnesium ion or a calcium ion.

pH of the mixture may be about 5.5 to about 9.5, about 5.5 to about 8.5, about 6.5 to about 8.5, about 6.5 to about 7.5, or about 7.0.

The incubating of the mixture may be performed at about 0° C. to about 40° C., about 10° C. to about 40° C., about 20° C. to about 40° C., about 30° C. to about 40° C., about 35° C. to about 40° C., or about 37° C. The incubating of the mixture may be performed for about 1 minute to about 24 hours, about 10 minutes to about 18 hours, about 20 minutes to about 12 hours, about 30 minutes to about 12 hours, about 1 hour to about 8 hours, about 1 hour to about 4 hours, about 2 hours to about 6 hours, or about 2 hours to about 4 hours.

The mixture may include about 0% (w/v) to about 10% (w/v), about 0% (w/v) to about 8% (w/v), about 0% (w/v) to about 6% (w/v), about 0% (w/v) to about 4% (w/v), or about 0% (w/v) to about 2% (w/v) of dimethyl sulfoxide (DMSO).

The method includes measuring an FP value of the mixture.

FP refers to a phenomenon, in which when a fluorescent material receives light having a specific orientation, it emits light having the same orientation as the received light, and at this time, the orientation of the emitted light differs from that of the received light according to characteristics including a molecular weight of the fluorescent material, viscosity of a solution including the target material, and density of the fluorescent material.

The method includes selecting the test material as an inhibitor of binding of CARD and LPS, when the measured FP value is lowered, as compared with that of a negative control not treated with the test material.

The method may further include calculating, from the measured FP value, an inhibition rate of binding of CARD and LPS. The inhibition rate of binding of CARD and LPS may be calculated as 50% inhibition such as $IC_{50}$.

The method may further include adding LPS and the test material to caspase-expressing cells; measuring caspase activity of the cells; and selecting the test material as an inhibitor of caspase activity by LPS, when the measured caspase activity is lowered, as compared with that of the negative control not treated with the test material.

The caspase-expressing cells may be transformed with a polynucleotide encoding caspase or a vector including the same.

The caspase activity may be measured using a substrate of caspase. The substrate may be, for example, 7-amino-4-methylcoumarin (AMC).

The method may be performed in vitro.

Another aspect provides a method of screening a therapeutic agent for inflammatory diseases or sepsis, the method including:
  incubating a mixture including a polypeptide, LPS, and a test material, the polypeptide including caspase CARD labeled with a fluorescent material;
  measuring a fluorescence polarization (FP) value of the mixture; and
  selecting the test material as the therapeutic agent for inflammatory diseases or sepsis, when the measured FP value is lowered, as compared with that of a negative control not treated with the test material.

The fluorescent material, caspase, CARD, lipopolysaccharide, test material, mixture, incubating, fluorescence polarization, and negative control are the same as described above.

The inflammatory disease may be selected from inflammatory bowel disease, multiple sclerosis, amyotrophic lateral sclerosis, Parkinson's disease, aging, and rheumatoid arthritis.

BRIEF DESCRIPTION OF THE DRAWINGS

The above and other aspects, features, and advantages of certain embodiments of the disclosure will be more apparent from the following description taken in conjunction with the accompanying drawings, in which.

Figure 1A:
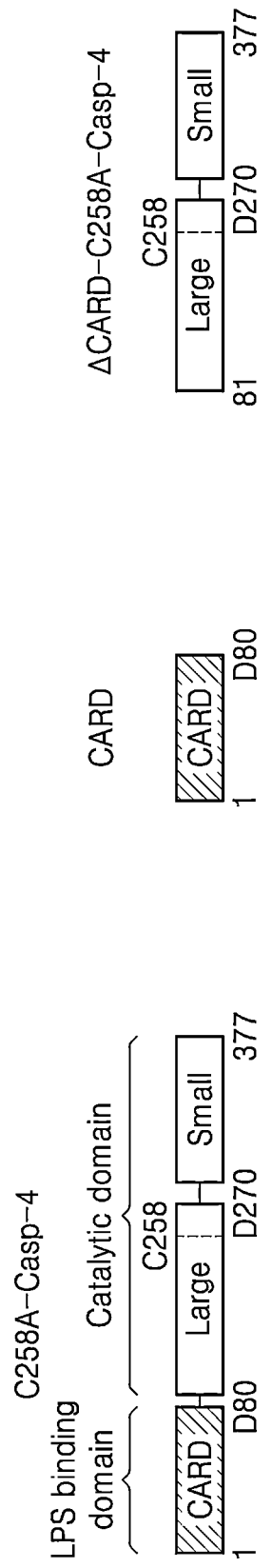
FIG. 1A shows illustrations of prepared constructs.

6C shows a graph showing activity of activated Casp-4 in the presence of four screened compounds.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, the present disclosure will be described in more detail with reference to Examples. However, these Examples are only for illustrating the present disclosure, and the scope of the present disclosure is not limited thereto.

Example 1. Measurement of Binding Affinity of Caspase-4 and LPS

(1) Preparation of Casp-4 Variants

Catalytically inactive full-length Casp-4 (1-377, C258A modification, referred to as 'C258A-Casp-4'), CARD(1-80), and CARD truncated Casp-4 (81-377, C258A modification, referred to as 'ΔCARD-C258A-Casp-4') were prepared.

Figure 2A:
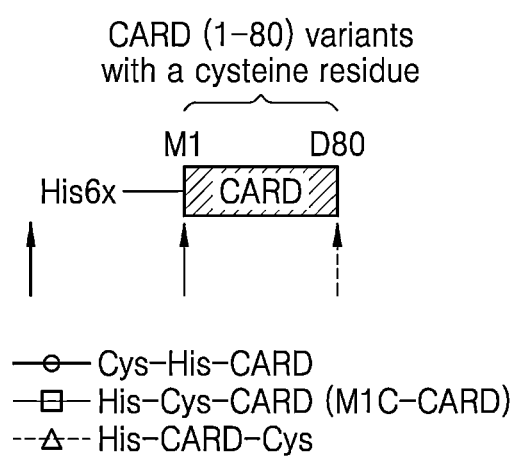
FIG. 2A shows an illustration of CARD variants in which cysteine is inserted.

Genes, each encoding C258A-Casp-4 or CARD, were cloned into NdeI and HindIII restriction sites of a pET28b vector having His6 tag at the N-terminus. ΔCARD-C258A-Casp-4, activated Casp-4(81-377)(p20/p10), three types of cysteine-inserted CARD(1-80) variants (Cys-His-CARD, His-Cys-CARD (M1C-CARD), and His-CARD-Cys) were prepared using a QUIKCHANGE Mutagenesis kit (Agilent Technologies). Schematic illustrations of the prepared constructs are shown in FIGS. 1A and 2A.

All constructs were transformed into CLEARCOLI BL21 (DE3)(Lucigen), respectively. When $OD_{600}$ reached 0.8, 0.2 mM IPTG (isopropyl-β-D-1-thiogalactopyranoside) induction was performed, and then cells were inoculated in an LB medium supplemented with 50 μg/mL of kanamycin and cultured at 18° C. overnight.

The cultured cells were harvested, and the harvested cells were sonicated in a buffer A (25 mM Tris-HCl pH 8.0, 300 mM NaCl, 20 mM imidazole) containing 5 mM beta-mercaptoethanol (β-mercaptoethanol: 2ME, Bio-Rad) (for full length Casp-4 C258A, 1% (v/v) TWEEN 20 (Bio-Rad) was supplemented). Thermostable CARD (1-80) and cysteine-inserted CARD variants were further incubated at 70° C. for 30 minutes after sonication. Each lysate was centrifuged at 4° C. and 12,000×g for 40 minutes, and each supernatant was loaded on a HISTRAP column (Cytiva) equilibrated with buffer A. The recombinant proteins were sequentially washed with 10 column volumes (CV) of buffer A, 10 CVs of buffer A and 0.1% (v/v) TWEEN 20, and 50 CVs of a mixture (a volume ratio of 9:1) of buffer A and buffer B (25 mM Tris-HCl pH 8.0, 300 mM NaCl, 300 mM imidazole). After washing, the recombinant proteins were eluted with a gradient of increasing concentration of buffer B. Thereafter, the recombinant proteins were purified using a SUPERDEX 200 gel-filtration column (Cytiva) equilibrated with buffer C (50 mM Tris-HCl pH 7.0, 150 mM NaCl) at 4° C.

(2) Analysis of Binding Affinity of Casp-4 and LPS

It was reported that caspase-4 (Casp-4) interacts with LPS through its CARD domain. To examine whether the interaction between CARD and LPS is related with binding affinity of Casp-4 and LPS, apparent equilibrium dissociation constants ($K_d^{app}$) of CARD and LPS were measured.

Apparent dissociation constants were measured by tryptophan fluorescence spectrometry. When LPS is bound, the fluorescence emission spectrum of the tryptophan residue in the LPS-binding protein shows a blue-shift and the fluorescence intensity tends to increase. Apparent dissociation constant values were calculated by analyzing the fluorescence emission spectra.

Figure 1B:
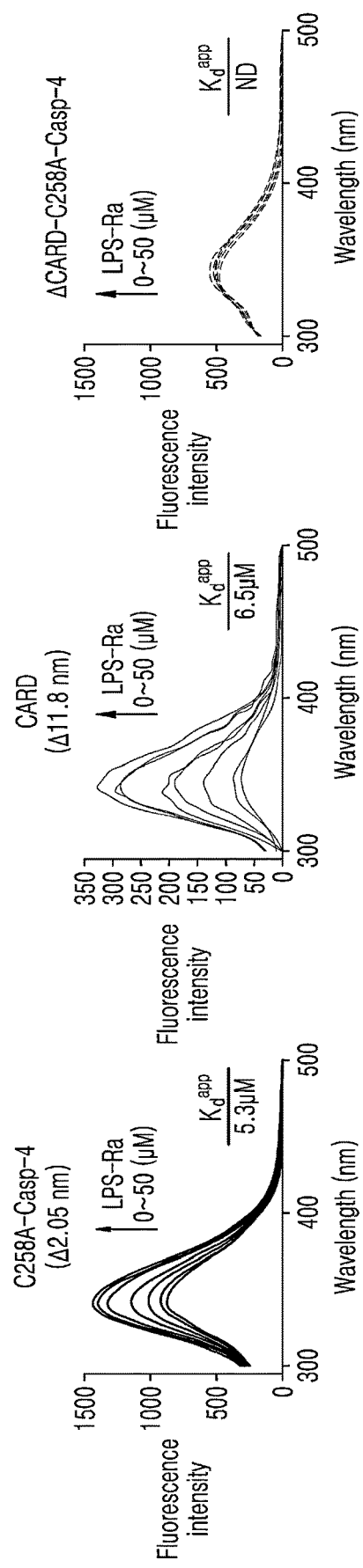
FIG. 1B shows graphs showing tryptophan emission spectra of full-length C258A-Casp-4, CARD, and ΔCARD-C258A-Casp-4 with LPS-Ra (0 μM to 50 μM)

Fluorescence spectra were obtained with a FluoroMate FS-2 fluorescence spectrophotometer (Sinco) equipped with a quartz cuvette with a 5 mm path length. 1 μM of the recombinant protein was mixed with increasing concentrations of LPS-Ra (in the range of 0 μM to 50 μM) in an HBS-E buffer (10 mM HEPES pH 7.5, 150 mM NaCl, 3 mM EDTA), and incubated at 37° C. for 30 minutes. The sample was excited at 280 nm, and emission spectra at 300 nm to 500 nm were recorded with an excitation/emission slit width of 2.5/5 nm, respectively. The fluorescence intensity of the sample was corrected by subtracting the background intensity of LPS alone. A difference in the fluorescence intensity at 334 nm was expressed as a function of LPS-Ra concentration, and the apparent equilibrium dissociation constant ($K_d^{app}$) was calculated from the nonlinear regression curve fit, as analyzed in GRAPHPAD PRISM 8. Graphs showing the emission spectra of the tryptophan residue in full-length C258A-Casp-4, CARD, and ΔCARD-C258A-Casp-4 in LPS-Ra (0 μM to 50 μM) are shown in FIG. 1B. As shown in FIG. 1B, upon LPS binding, blue shifts were found (2.05 nm and 11.8 nm, respectively) and the fluorescence intensity increased in a concentration-dependent manner. The $K_d^{app}$ values calculated from the fluorescence spectra of C258A-Casp-4 and CARD were 5.3±0.5 μM and 6.5±0.8 μM, respectively.

Figure 1C:
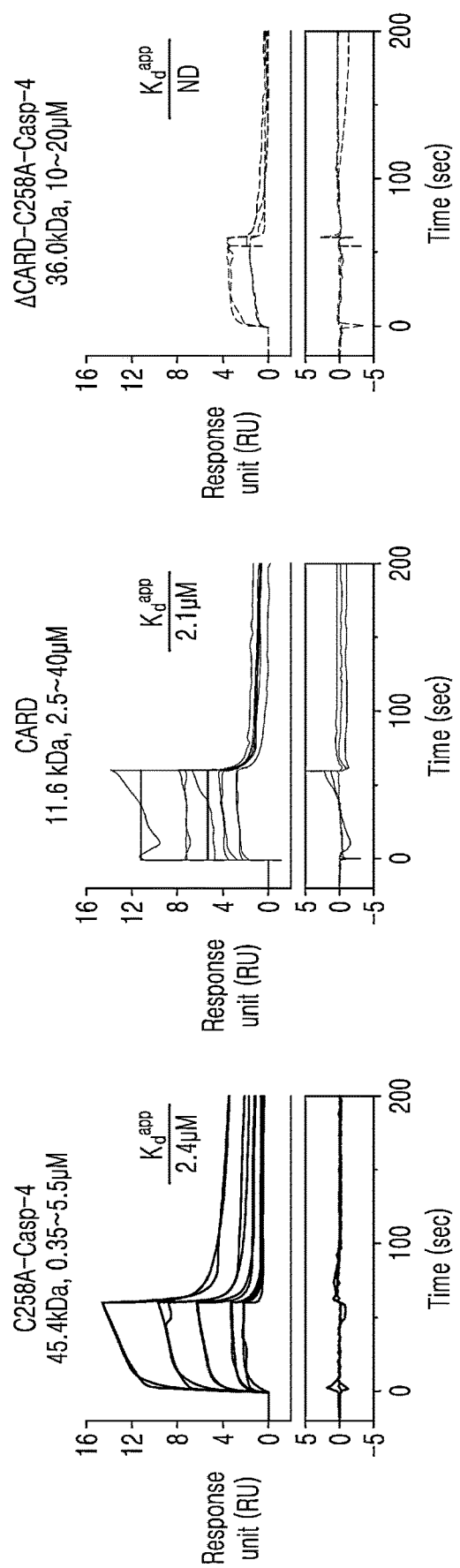
FIG. 1C shows SPR sensorgrams of full-length C258A-Casp-4, CARD, and ΔCARD-C258A-Casp-4 binding to E. coli LPS(O55:B5) immobilized on a CM5 chip sensor.

In addition, the binding affinity between Casp-4 and LPS was determined by a surface plasmon resonance (SPR) experiment. The SPR experiment was performed at 25° C. using a BIACORE T200 (Cytiva). A filtered and degassed running buffer (HBS-E) was prepared prior to use. Amine-derived LPS O55:B5 (NH-LPS, Sigma-Aldrich) was prepared by a method described in P. T. Wong et al., J Mater Chem B, 2015, 3, 1149-1156, herein incorporated by reference. NH-LPS was immobilized on a CM5 sensor chip (Cytiva) using an amine coupling method (480 RU), and blocked with 1 M ethanolamine (pH 8.5). Purified proteins of the indicated concentration were injected, and the resulting sensorgrams were analyzed using a BIACORE T200 Evaluation software. The SPR sensorgrams are shown in FIG. 1C. As shown in FIG. 1C, the dissociation constants of C258A-Casp-4 and CARD were 2.4 μM and 2.1 μM, respectively.

However, as shown in FIGS. 1B and 1C, the binding between ΔCARD-C258A-Casp-4 and LPS was not identified in both methods.

Therefore, it was confirmed that CARD may be used in an assay to monitor the binding between LPS and Casp-4.

(3) Fluorescent Dye Labeling and Fluorescence Polarization Analysis of CARD Variants The labeling efficiency of each CARD was evaluated using ALEXA FLUOR 488 which is a thiol-reactive fluorescent dye, and the dynamic range of the fluorescence polarization signal of the construct upon binding to LPS was measured.

To evaluate the labeling efficiency of CARD, variants (His-Cys-CARD, M1C-CARD) including cysteine at the N-terminal (Cys-His-CARD), at the C-terminal (His-CARD-Cys), or between the N-terminal His6 tag and CARD were prepared (FIG. 2A), using the fact that CARD does not include a cysteine residue.

The cysteine-inserted CARD variants were incubated overnight at 4° C. with the addition of buffer C supplemented with a 5-fold molar excess of ALEXA FLUOR 488 C5 maleimide (Invitrogen) and a 10-fold molar excess of TCEP. Dyes not used for labeling were removed by using a PD-10 desalting column (Cytiva) and a 10K centrifugal filter (Millipore) until no dye was detected in the filtrate. The labeled CARD was identified by SDS electrophoresis (FIG. 2C).

The labeling efficiency was calculated according to the Lambert-Beer law using absorbance measured at 280 nm and 489 nm using a UV/Vis spectrophotometer (BIOCHROM LIBRA S22). Absorbance at 280 nm provided by Alexa-Fluor 488 was corrected using a correction factor of 0.11.

The labeling efficiency is shown in Table 1.

TABLE 1

| Cysteine-inserted CARD variant | Labeling efficiency (%) |
| --- | --- |
| Cys-His-CARD | 24% |
| His-Cys-CARD (M1C-CARD) | 86% |
| His-CARD-Cys | 7.8% |

Figure 2B:
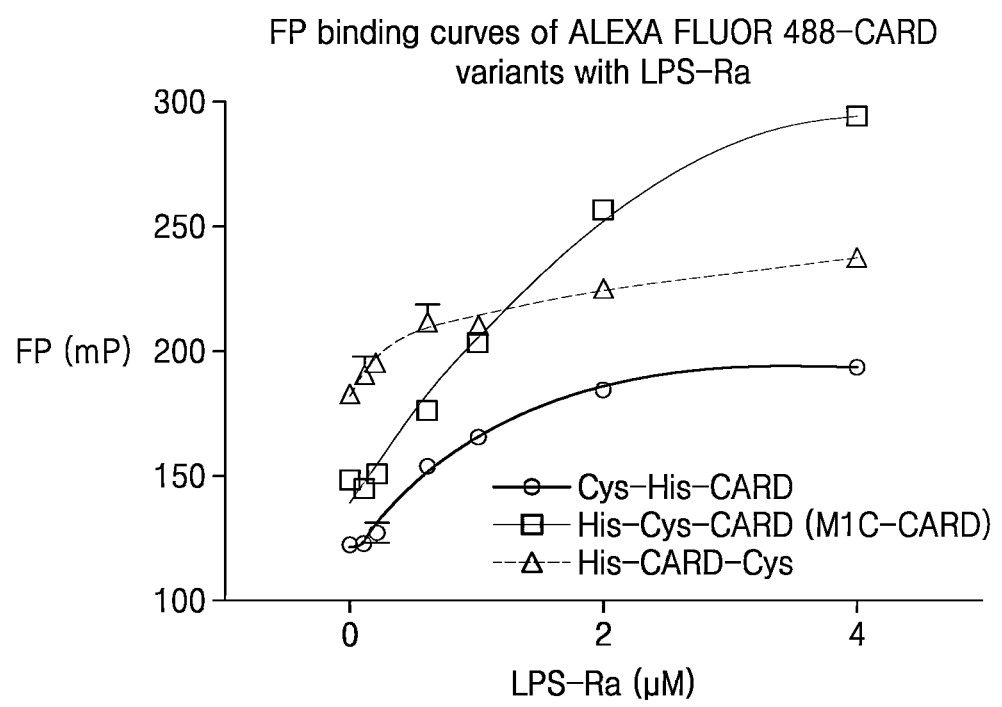
FIG. 2B shows a graph showing an FP binding assay of ALEXA FLOUR 488-labeled CARD variants for LPS.
Figure 2C:
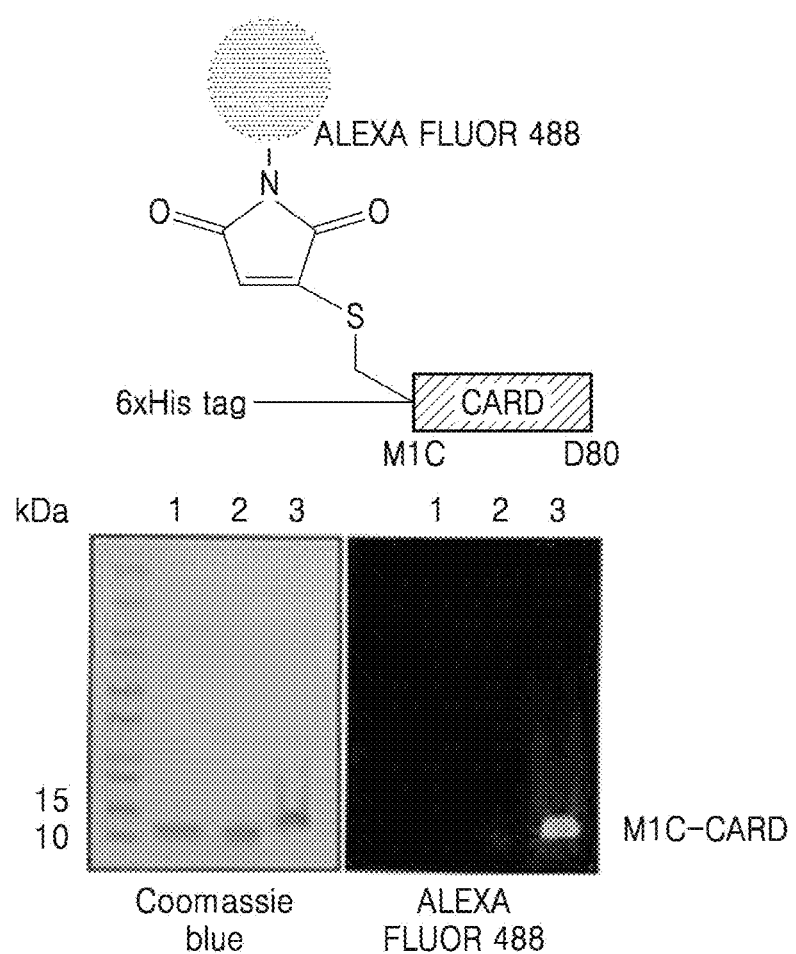
FIG. 2C shows an illustration of an ALEXA FLOUR 488-labeled CARD variant and Coomassie blue staining (left) and fluorescence (right) images of an SDS-PAGE gel of M1C-CARD purified by Ni-NTA column chromatography (lane 1) and SUPERDEX 200 column chromatography (lane 2) and after labeling with ALEXA FLUOR 488 (lane 3)
Figure 2D:
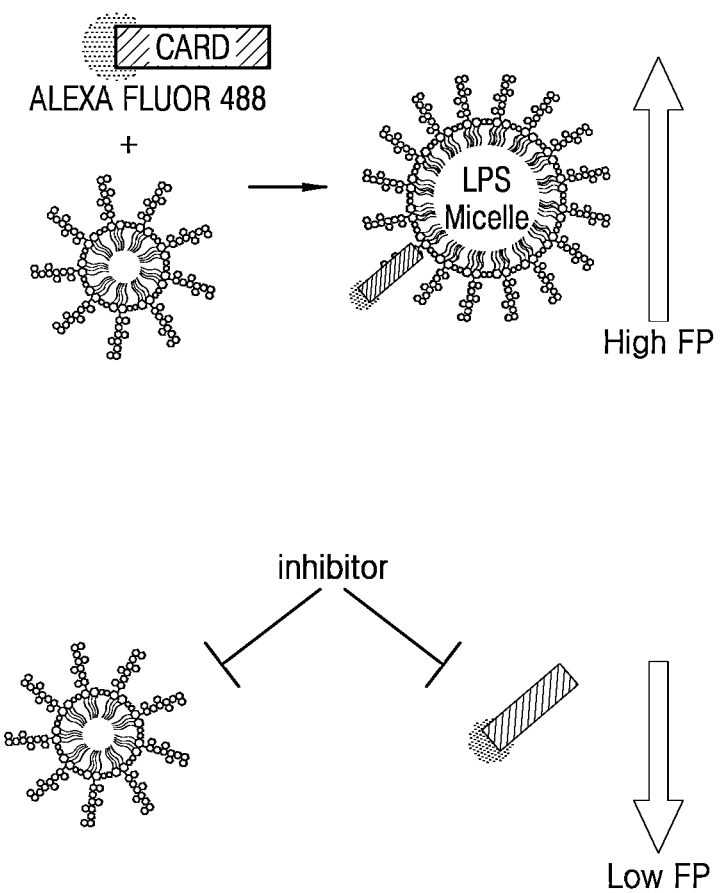
FIG. 2D shows illustrations of binding of CARD and LPS and a method of screening for inhibitors using the same.

To examine whether it is possible to screen agents inhibiting binding between CARD and LPS through fluorescence polarization of the CARD variants, a fluorescence polarization-based analysis between CARD and LPS was performed (FIG. 2B). Binding between CARD and LPS and use thereof for screening of inhibitors' are illustrated in FIG. 2D.

Fluorescence polarization (FP) was measured with an APPLISKAN microplate reader (ThermoFisher) using 485 nm excitation and 535 nm emission filters. The FP value was calculated according to the following equation: FP (mP)= $1000 \times (I_s - G \times I_p)/(I_s + G \times I_p)$. In the equation, $I_s$ represents a parallel (equivalent) emission intensity, $I_p$ represents a perpendicular emission intensity, and G represents a lattice coefficient 0.877.

Figure 2E:
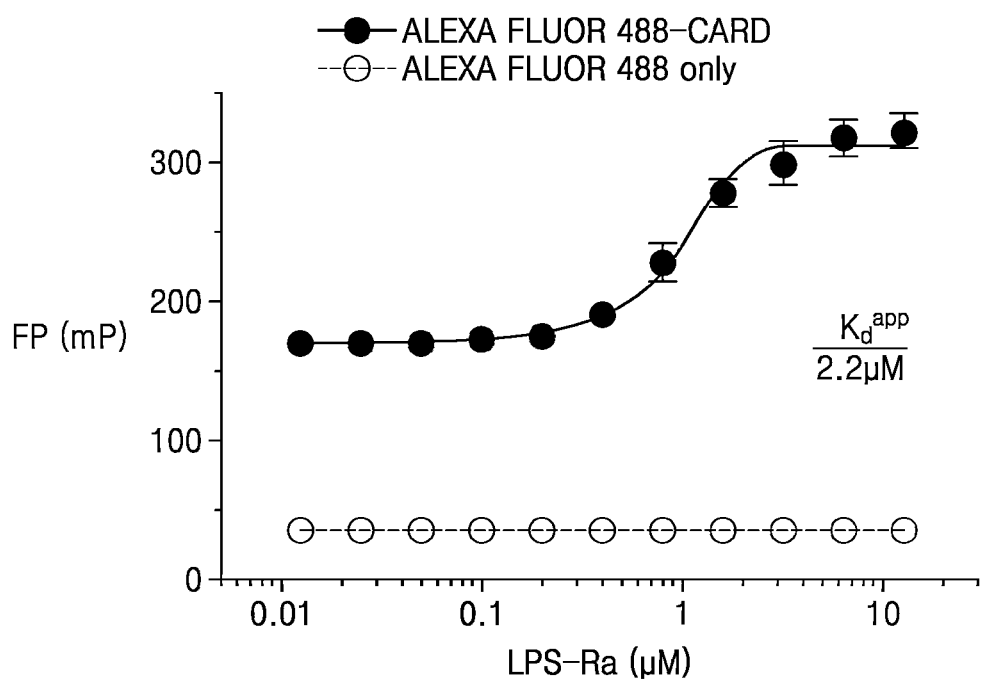
FIG. 2E shows an FP binding curve of ALEXA FLUOR 488-CARD or ALEXA FLUOR 488 alone (dye) depending on LPS concentrations.

FP binding assay was performed by adding 200 μL of a reaction mixture to each well of a black 96-well plate (SPL Life Sciences). The reaction mixture includes 50 nM ALEXA FLUOR 488-CARD (tracer) with increasing concentrations of LPS-Ra (in the range of 0 μM to 12.8 μM, a molecular weight of LPS-Ra is assumed to be 3,835 g/mole, Sigma-Aldrich) in a buffer C or an indicated buffer. The reaction mixture was incubated at 37° C. for 30 minutes to 4 hours before reaction. FP values are expressed as a function of LPS-Ra concentration. FP binding curves of His-Cys-CARD (ALEXA FLUOR 488-CARD) or ALEXA FLUOR 488 alone (dye) with respect to the concentrations of LPS are shown in FIG. 2E.

Apparent equilibrium dissociation constants ($K_d^{app}$) were calculated from the nonlinear regression curve fit, as analyzed in GRAPHPAD PRISM 8 from the FP binding curves.

Reproducible separation of the FP values for binding of LPS and ALEXA FLOUR 488-CARD and controls at different concentrations (0% to 10%) of DMSO (Sigma-Aldrich) were evaluated using Z' factor. The Z' factor was calculated by the following equation: $1-(3SD_s+3SD_p)/|\mu_s-\mu_p|$. In the equation, $SD_s$ and $SD_p$ represent standard deviations of a sample and a positive control (without LPS), and $\mu_s$ and $\mu_p$ represent averages of FP values obtained from the sample and the positive control (without LPS), respectively.

As shown in Table 1 and FIG. 2B, His-Cys-CARD showed the highest labeling efficiency (about 86%), showed the largest difference in polarization signal, and showed a sigmoidal FP binding curve with increasing fluorescence intensity. The $K_d^{app}$ value determined for ALEXA FLOUR 488-CARD and LPS was 2.2±0.2 μM when 50 nM ALEXA FLOUR 488-CARD was used (FIG. 2E).

Therefore, it was confirmed that ALEXA FLUOR 488-labeled His-Cys-CARD (ALEXA FLOUR 488-CARD) had a detectable wide window for the binding between CARD and LPS, and thus ALEXA FLOUR 488-CARD was selected as a tracer for high-throughput inhibitor screening assays.

(4) Optimization of FP Analysis Method for Application to High-Throughput Inhibitor Screening Assay To optimize high-throughput screening (HTS) of inhibitors, additives, incubation time, pH, and DMSO concentrations were optimized.

Figure 3A:
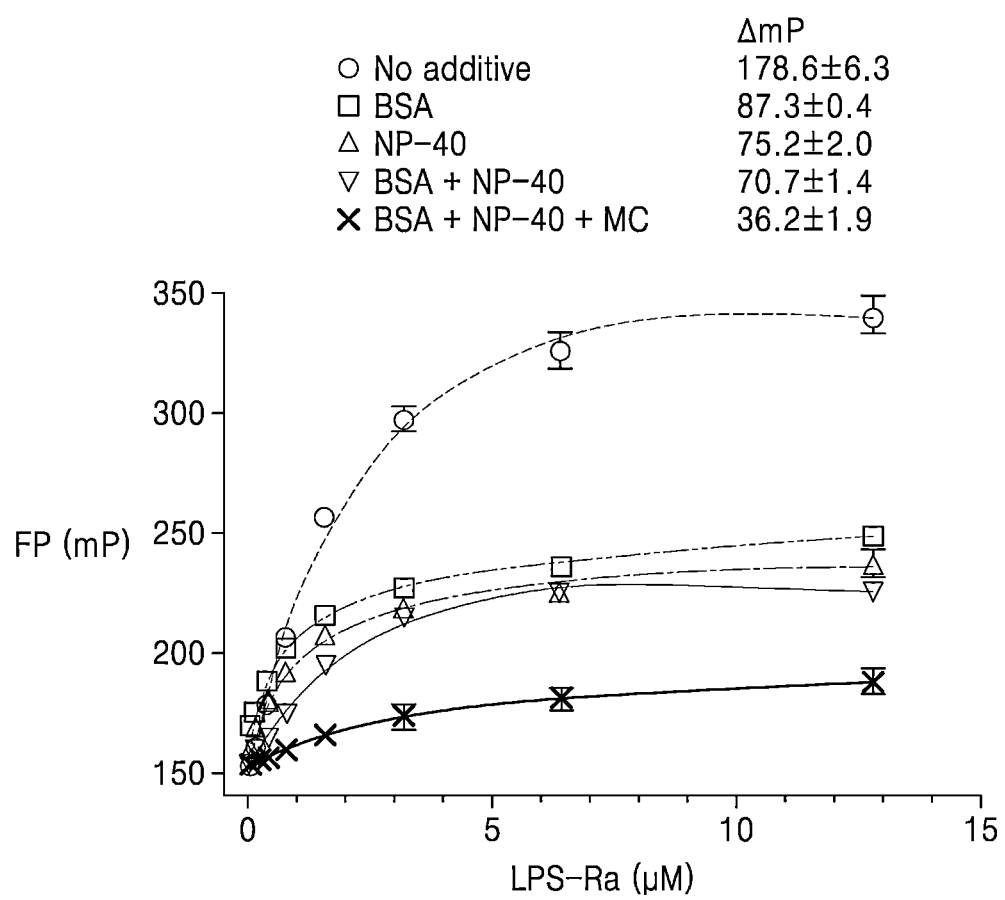
FIGS. 3A to 3E show FP binding curves with respect to additives, incubation time, pH, different concentrations of LPS-Ra, and different concentrations of DMSO, respectively.
Figure 3B:
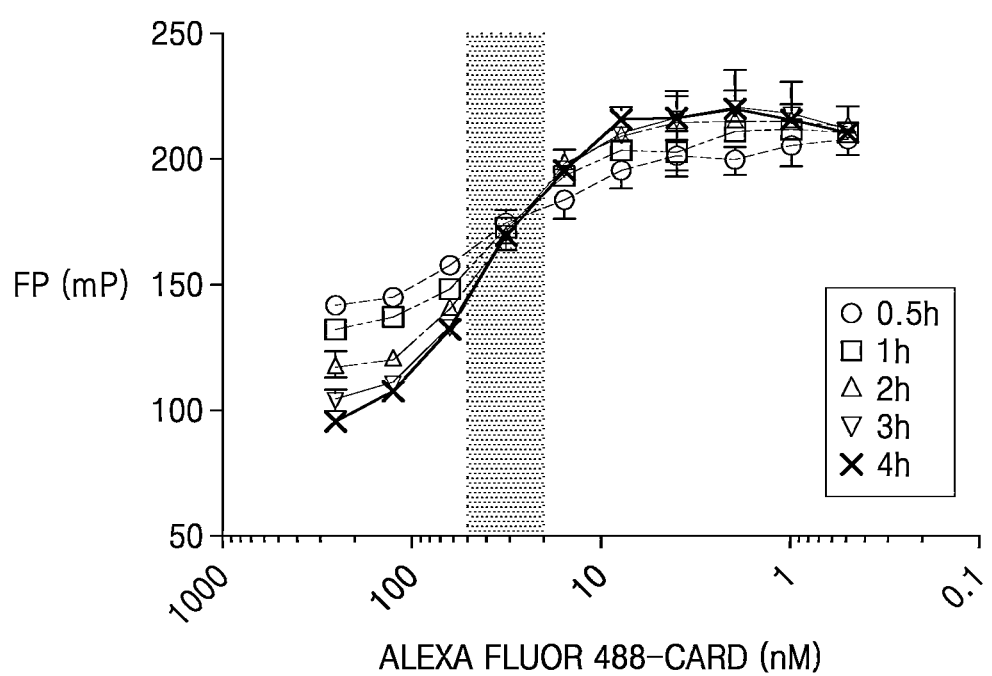
Figure 3C:
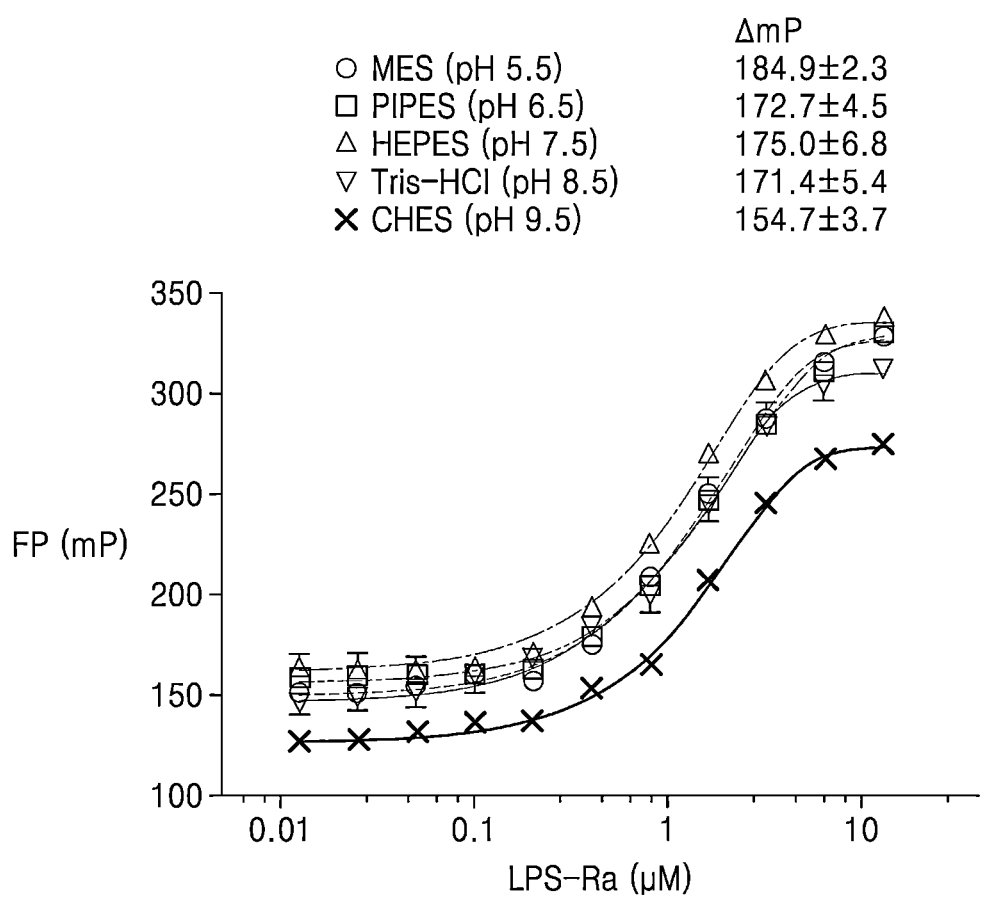
Figure 3D:
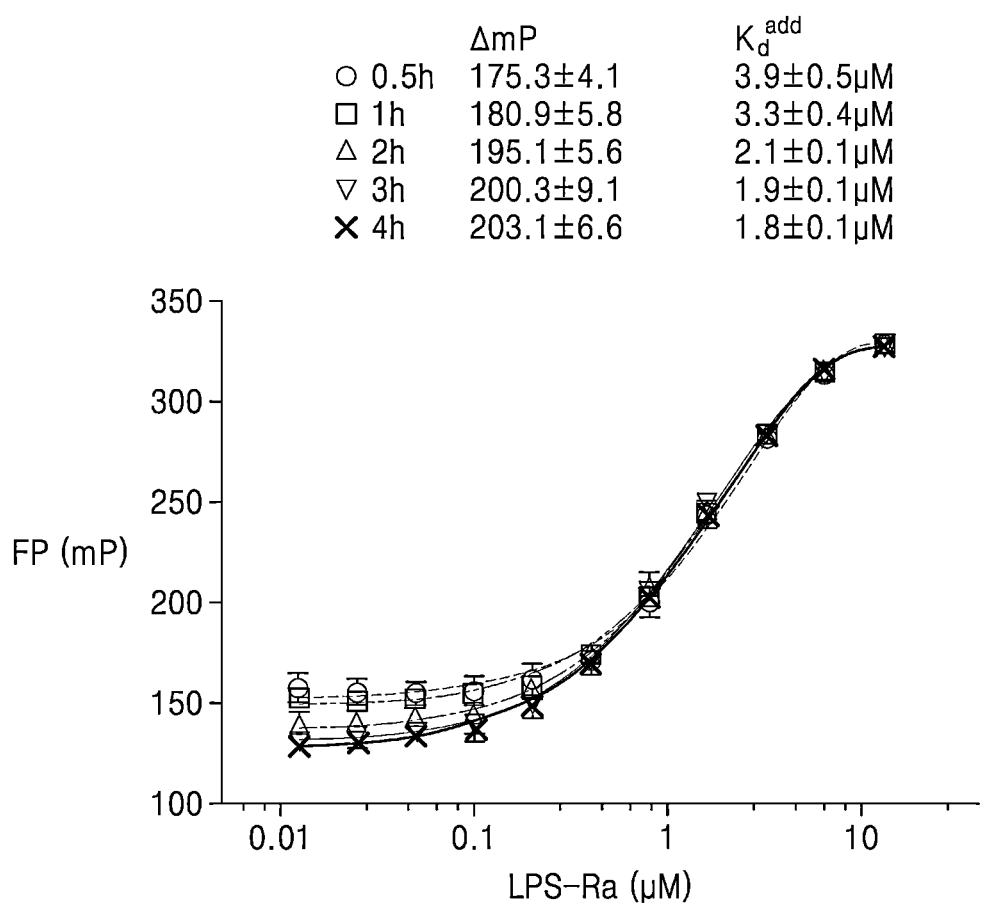
Figure 3E:
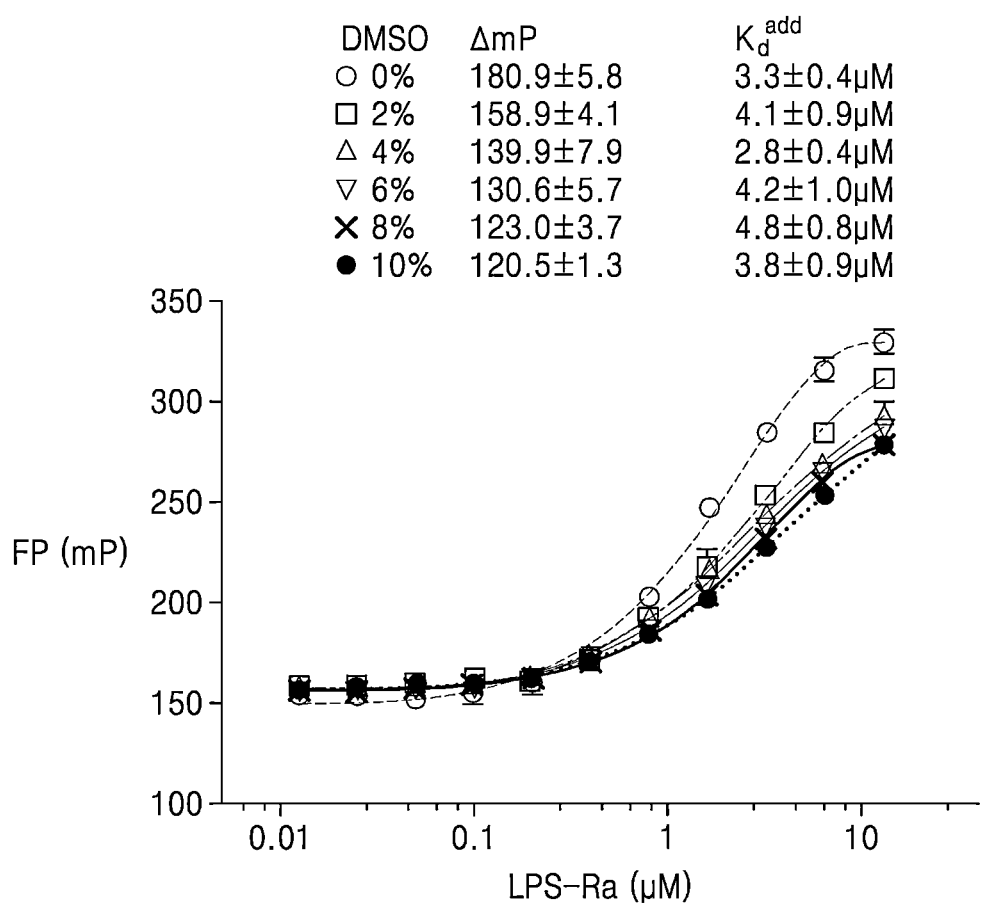

An FP binding curve from FP values measured with buffer C (50 mM Tris-HCl pH 7.0, 150 mM NaCl) supplemented with additives such as 0.1 mg/mL BSA, 0.01% NP-40, or 1 mM MC ($MgCl_2+CaCl_2$) is shown in FIG. 3A. An FP binding curve from FP values measured by incubating ALEXA FLOUR 488-CARD serially diluted with buffer C for 0.5 hours to 4 hours is shown in FIG. 3B (grey area: range of 20 nM to 50 nM). An FP binding curve from FP values measured with buffers of different pHs is shown in FIG. 3C. An FP binding curve from FP values measured by incubating different concentrations of LPS-Ra in buffer C for 0.5 hours to 4 hours is shown in FIG. 3D. An FP binding curve from FP values measured with buffer C supplemented with different concentrations of DMSO is shown in FIG. 3E. In addition, LPS-Ra concentration-dependent Z' factor was evaluated in buffer C supplemented with 0% to 10% DMSO. Unless otherwise mentioned, reactions were incubated at 37° C. for 1 hour.

Figure 3F:
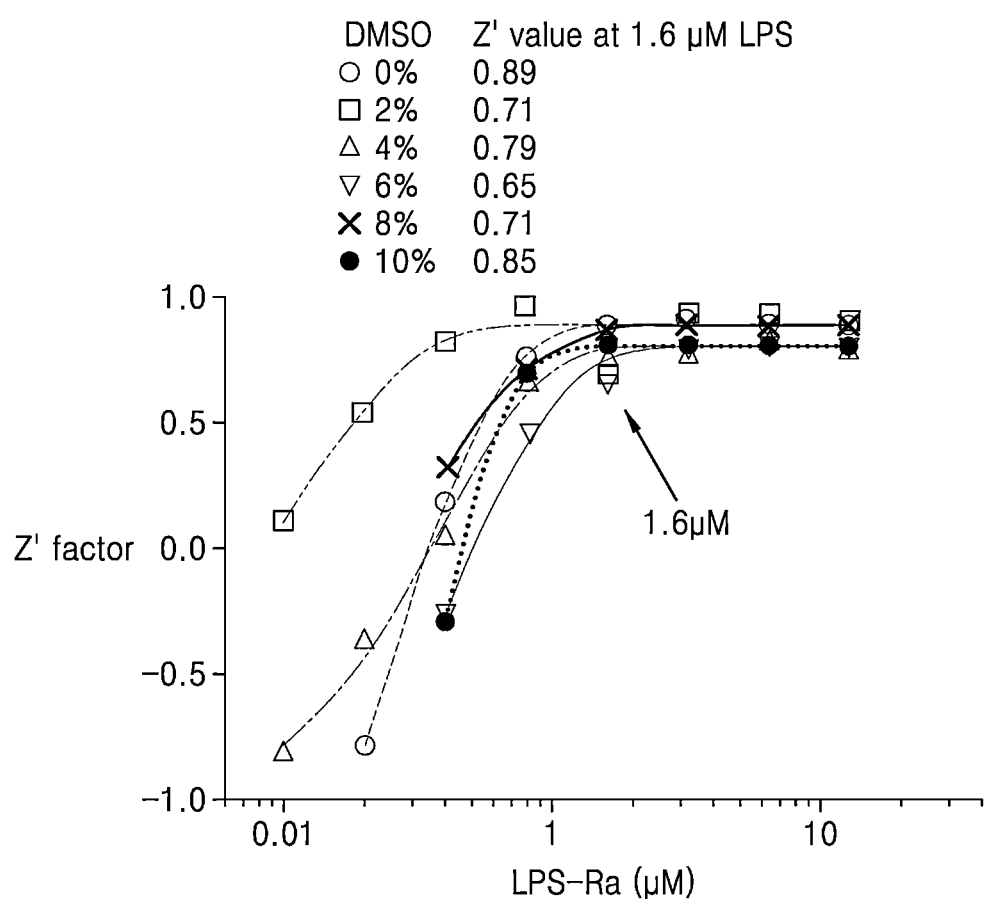
FIG. 3F shows a graph showing Z' factor depending on 0% to 10% DMSO.

As shown in FIG. 3A, the binding of CARD and LPS was inhibited by the presence of BSA, NP-40, or divalent cations. Based on the results of FIGS. 3B to 3D, the assay was set up with use of 50 nM ALEXA FLUOR 499-CARD at pH 7.0, 150 mM NaCl, and 37° C. In addition, as shown in FIGS. 3E and 3F, as the concentration of DMSO increased, the dynamic range of the FP value slightly decreased, but the $K_d^{app}$ value maintained in the similar range up to 10% DMSO, and 1.6 μM of LPS-Ra was selected as a minimum concentration to yield a Z' coefficient of ~ 0.7, which is a statistical cutoff value providing reproducible separation between target and control within a wide range of DMSO concentrations.

(5) Screening for Inhibitor of Binding of CARD and LPS

After constructing HTS, a library of 1,443 FDA-approved drugs was screened to select hit compounds inhibiting 50% of FP signal.

For the HTS method, 0.8 μL of FDA-approved drug (2.5 mM in DMSO, Selleckchem) was added to each well of a 96-well plate containing 50 nM tracer and 1.6 μM LPS-Ra using a pipetting device (Mosquito, sptlabtech) to prepare a final volume of 200 μL per well. Each plate contained a negative control (DMSO with LPS) and a positive control (DMSO without LPS). FP was measured using APPLIS-KAN after incubation at 37° C. for 1 hour. A final inhibition rate was calculated by the following equation: inhibition rate (%)=100×((mP$_{negative}$−mP$_{test\ compound}$)/(mP$_{negative}$−mP$_{positive}$)). In the equation, mP$_{negative}$ represents an FP value of a negative control, mP$_{positive}$ is an FP value of a positive control, and mP$_{test\ compound}$ is an FP value of a sample containing a test compound. The 50% inhibition rate was arbitrarily chosen as a threshold.

Figure 4:
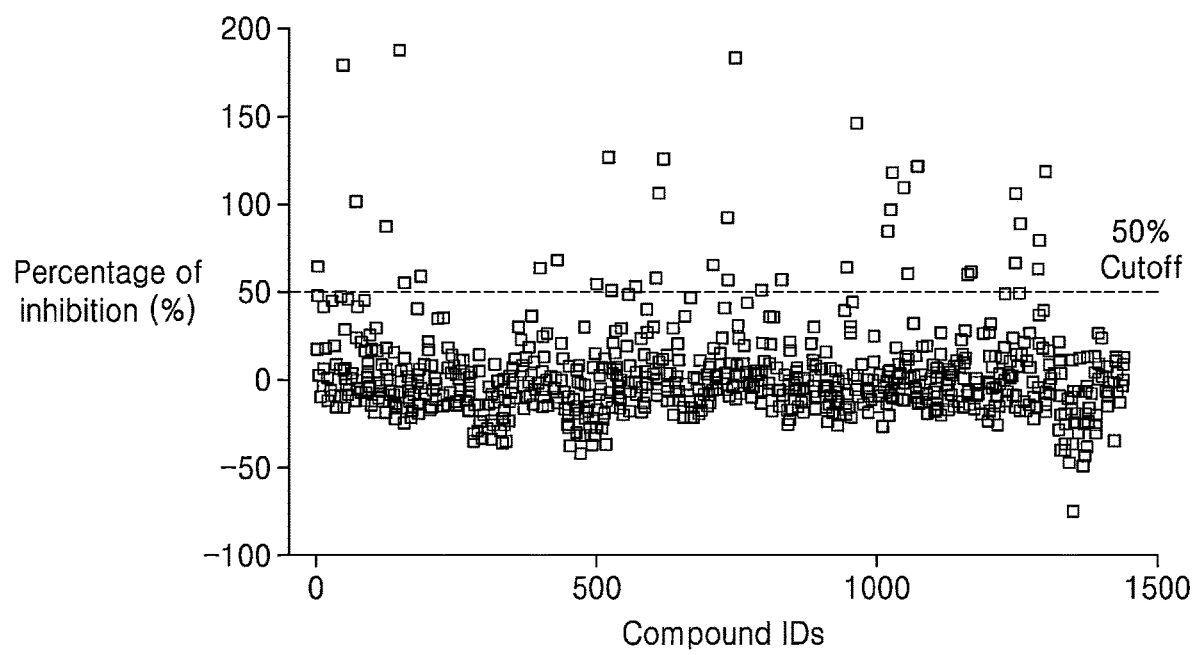
FIG. 4 shows a graph showing results of screening of a library of FDA-approved drugs (1,443 drugs) for inhibition of binding of CARD and LPS.
Figure 5A:
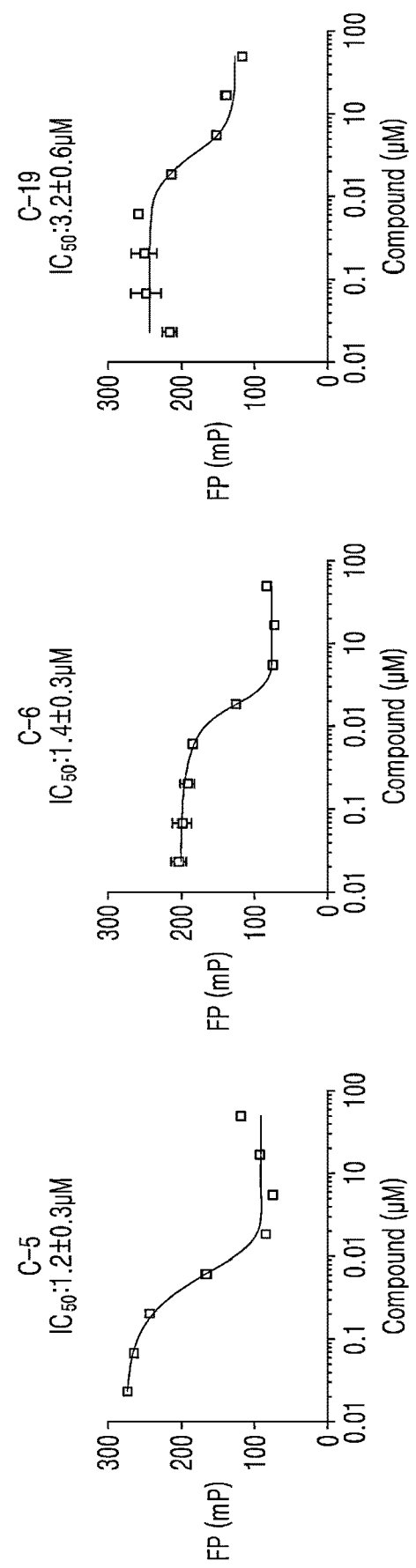
FIGS. 5A to 5C show graphs showing results of FP competition assays of nine screened hit compounds.
Figure 5B:
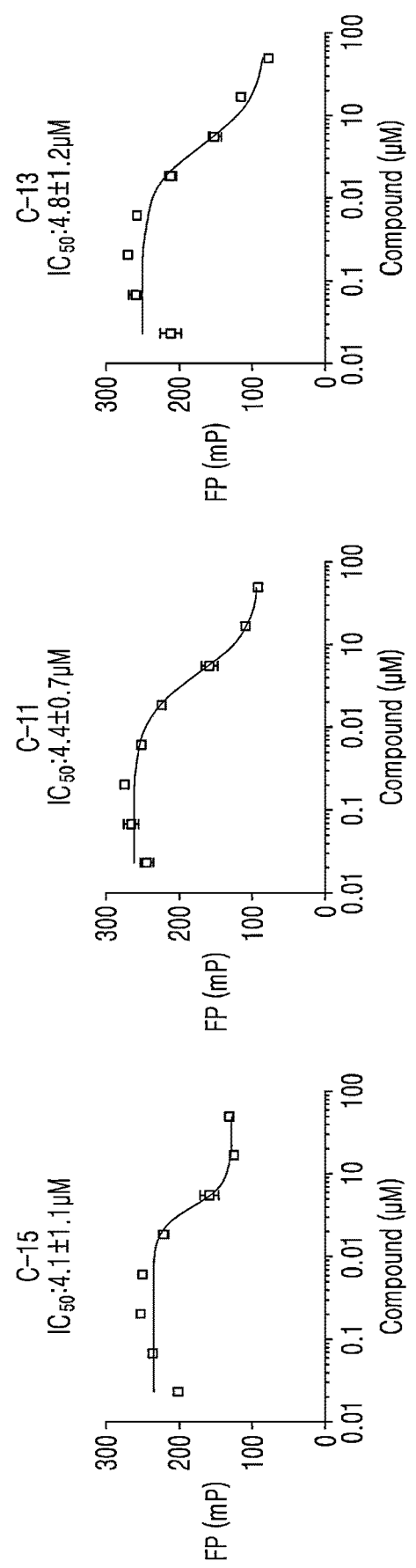
Figure 5C:
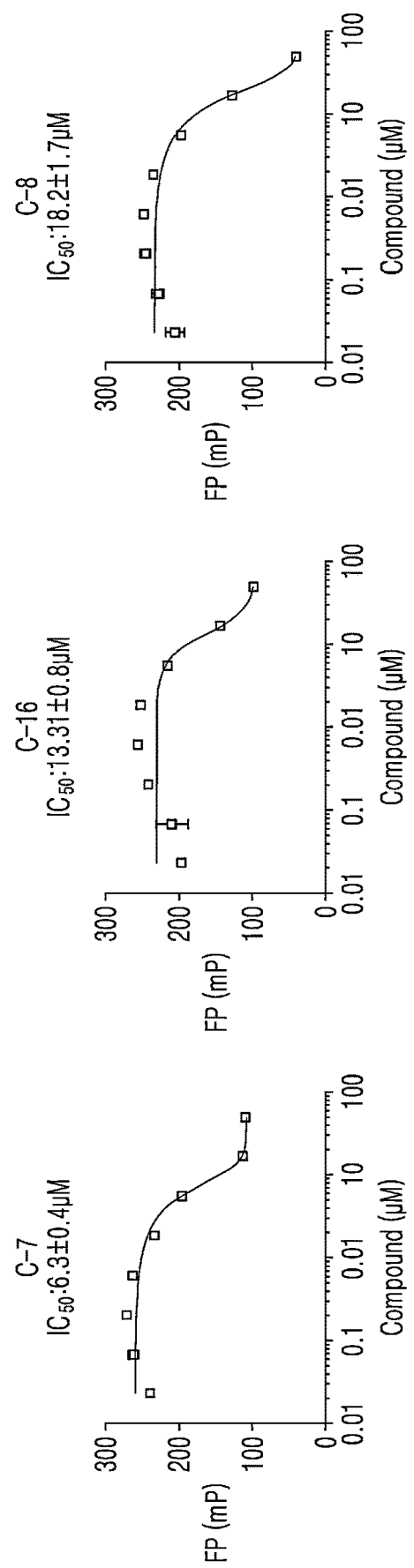

The results of screening by the HTS method are shown in FIG. 4. Among the hit compounds, 32 compounds were selected (hit rate: about 2.2%), excluding 25 pan-assay interference compounds (PAINS) and fluorescence quenchers.

IC$_{50}$ value of each hit compound was determined using an FP competition assay in the presence of the hit compound serially diluted from 50 μM to 0.022 μM with 6.4 μM (about twice the K$_d^{app}$ value) of LPS-Ra and 0 nM of ALEXA FLOUR 488-CARD. In detail, the FP competition assay was performed by mixing 50 nM of tracer, 6.4 μM of LPS-Ra, and 3-fold serially diluted hit compound (50 μM to 0.022862 μM) in buffer C. The mixture was incubated at 37° C. for 1 hour before measurement. FP values were expressed as a function of compound concentrations, and IC$_{50}$ values were obtained from a sigmoidal curve fit, as analyzed in GRAPH-PAD PRISM 8.

As shown in FIGS. 5A to 5C, 9 compounds (C-5: Crystal violet, C-6: Mitoxantrone, C-19: Entrectinib, C-15: Sotrastaurin, C-11: Eltrombopag Olamine, C-13: Enzastaurin, C-7: Eltrombopag, C-16: Ceritinib, C-8: Ethacridine lactate) out of 32 compounds showed FP signal decreases in a concentration-dependent manner within the IC$_{50}$ value of μM level.

(6) Inhibition of Casp-4 Activity by Screened Compounds

Autolytic activation of Casp-4 requires interaction with cytoplasmic LPS, and therefore, it was examined whether, when a hit compound inhibits the interaction between LPS and CARD, subsequent Casp-4 activation and its catalytic activity are inhibited by the hit compound.

Genes, each encoding a wild-type Casp-4 or a C258A-Casp-4 inactive variant, were cloned into KpnI and XbaI restriction sites of a p3xFLAG-CMV-10 vector. HEK293T cells cultured in a DMEM medium (Welgene) supplemented with 10% (v/v) heat-inactivated FBS (Gibco), 100 U/mL penicillin and 100 U/mL streptomycin were transfected with each construct using LIPOFECTAMINE 2000 (ThermoFisher). 24 hours after transfection, cells were re-inoculated into a black, flat-bottomed 96-well culture dish (SPL life sciences) at a density of 10$^5$ cells per well. After incubation for 2 hours for cell adhesion, the culture supernatant was replaced by an activity assay buffer [(0.01% (w/v) digitonin(Sigma-Aldrich), 10 mM DTT, 100 μM Ac-WEHD-AMC(Enzo-life science), 10 μM LPS-Ra, and 50 μM of the hit compound, or buffer C supplemented with an equal volume of DMSO]. For the assay of active Casp-4 (p20/p10), 1 μM of purified p20/p10 was assayed using the same assay buffer. Hydrolysis of fluorescent 7-amino-4-methylcoumarin (AMC, Sigma-Aldrich) was monitored with APPLISKAN at room temperature using 326 nm excitation and 460 nm emission filters at the predetermined time intervals. The amount of free AMC hydrolyzed by Casp-4 was calculated using a standard curve prepared with AMC serially diluted with the assay buffer containing each hit compound.

Figure 6A:
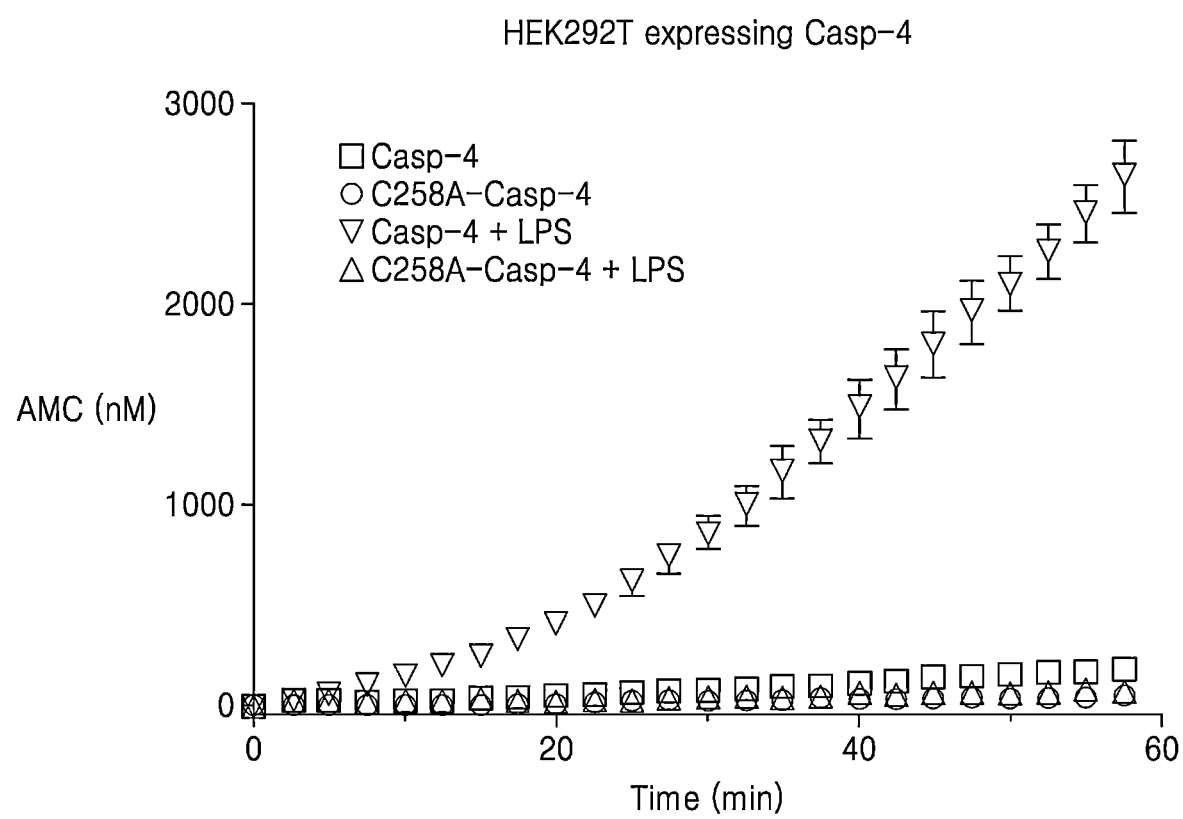
FIG. 6A shows a graph showing Casp-4 activity depending on the presence of LPS in Casp-4-expressing HEK293T cells.
Figure 6B:
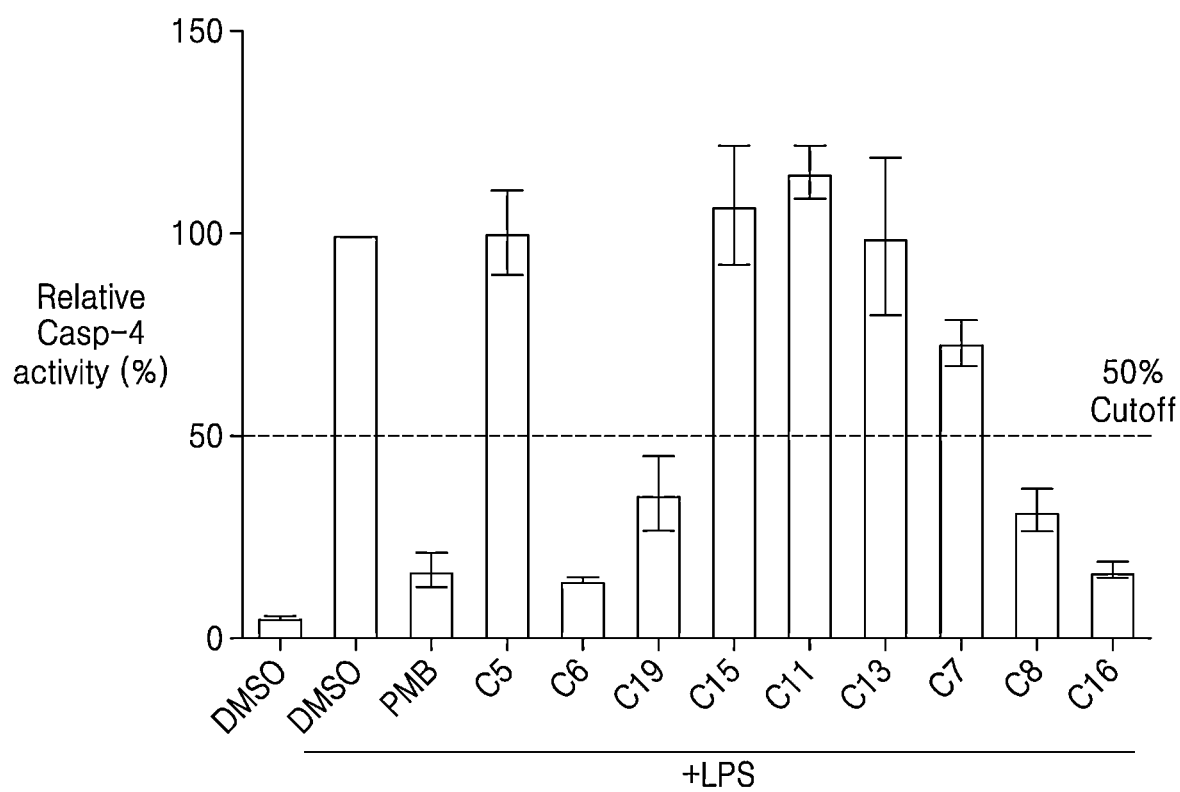
FIG. 6B shows a graph showing inhibition of Casp-4 activity in the presence of LPS and screened hit compounds in which the dashed line indicates 50% inhibition, and FIG.
Figure 6C:
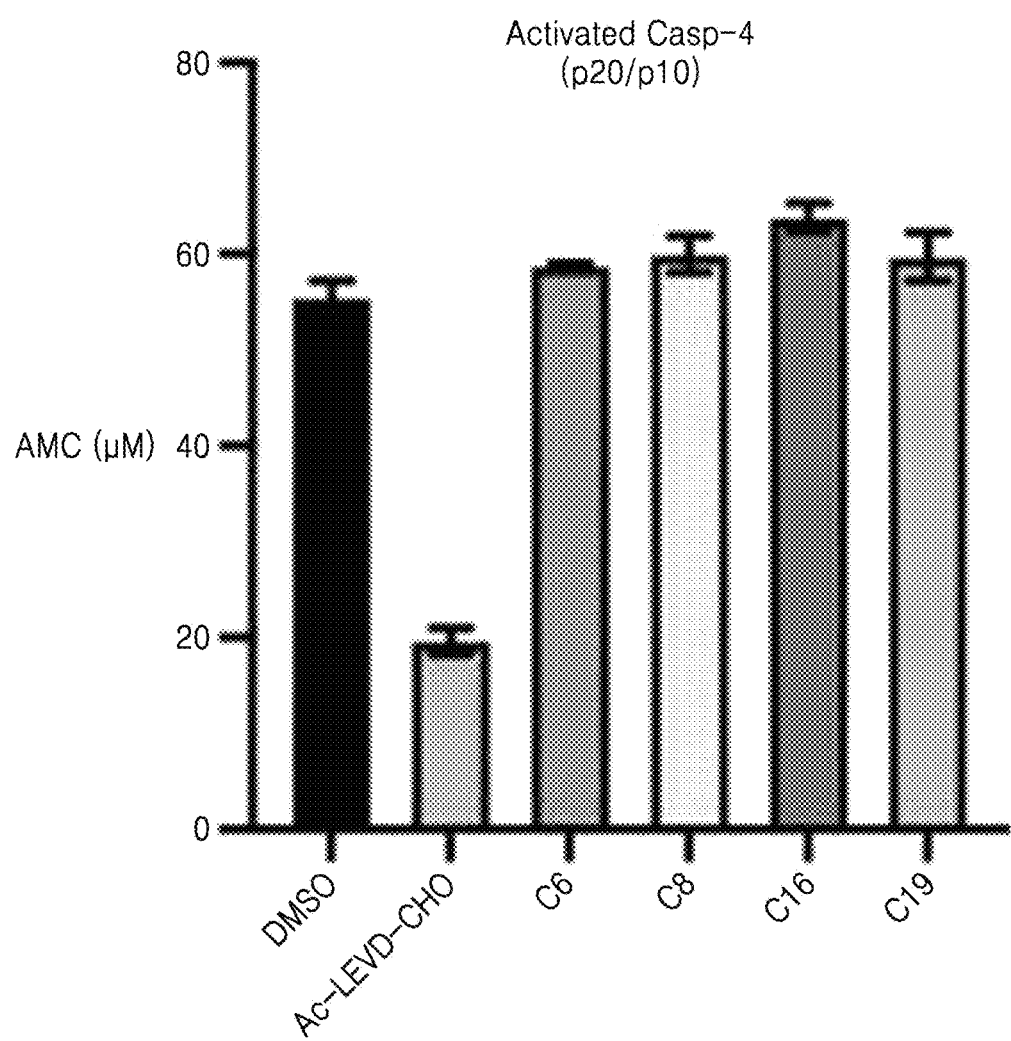

Activities of the full-length Casp-4 and activated p20/p10 Casp-4 in the presence of LPS (activator) with or without the screened compound (inhibitor) are shown in FIGS. 6A to 6C.

As shown in FIG. 6A, Casp-4 or C258A-Casp-4 had no activity in the absence of LPS, whereas the activity of Casp-4 dramatically increased in the presence of LPS. Based on this, the Casp-4 inhibitory effects of 9 hit compounds were examined, and the results are shown in FIG. 6B. DMSO as a negative control and LPS-sequestering antibiotic polymyxin B (PMB) as a positive control were used. As shown in FIG. 6B, 4 hit compounds out of 9 hit compounds inhibited Casp-4 activity by 50% or more at a concentration of 50 μM. However, when activated Casp-4 (P20/p10) was used, the Casp-4 inhibitory effect by the compound was not identified (FIG. 6C).

Therefore, it was found that it is possible to screen inhibitors specifically inhibiting the binding of LPS and CARD, thereby inhibiting the activity of Casp-4, through the established HTS method, in order to develop drugs for treatment of inflammation and sepsis caused by LPS.

According to the method of screening an inhibitor of caspase activity by lipopolysaccharide and the method of screening a therapeutic agent for inflammatory diseases or sepsis using the same, a caspase-4-specific inhibitor may be developed.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of screening for an inhibitor of caspase-4 activity, wherein the caspase-4 is activated by lipopolysaccharide (LPS), the method comprising:
   incubating a mixture comprising a caspase-4-derived polypeptide, lipopolysaccharide (LPS), and a test material, wherein the caspase-4-derived polypeptide comprises a caspase activation and recruitment domain (CARD) labeled with a fluorescent material, wherein the CARD has an amino acid sequence selected from the group consisting of SEQ ID NOs: 1, 7 and 9, wherein a pH of the mixture is 5.5 to 9.5 and the incubation is conducted at 0° C. to 40° C.;
   measuring a fluorescence polarization (FP) value of the mixture;
   selecting the test material as an inhibitor of binding of CARD and LPS, when the measured FP value is lowered, as compared with that of a negative control not treated with the test material; and
   calculating, from the measured FP value, an inhibition rate of binding of CARD and LPS;
   wherein the CARD has a peptide tag at the N-terminus and having cysteine (Cys) inserted between the C-terminus of the peptide tag and the N-terminus of the CARD.

2. The method of claim 1, wherein the fluorescent material is conjugated through cysteine.

3. The method of claim 1, wherein the mixture does not comprise bovine serum albumin (BSA), a surfactant, a divalent cation, or a combination thereof.

4. The method of claim 1, wherein pH of the mixture is 7.0.

5. The method of claim 1, wherein the incubating of the mixture is performed at 37° C.

6. The method of claim 1, wherein the mixture comprises 0% (w/v) to 10% (w/v) of dimethyl sulfoxide (DMSO).

7. The method of claim 1, further comprising:
   after said selection of the test material, adding LPS and the test material to caspase-expressing cells;

measuring caspase activity of the cells; and
selecting the test material as an inhibitor of caspase activity in said cells, when the measured caspase activity is lowered, as compared with that of a negative control not treated with the test material.

\* \* \* \* \*

SEQUENCE LISTING

```
<160> NUMBER OF SEQ ID NOS: 16

<210> SEQ ID NO 1
<211> LENGTH: 377
<212> TYPE: PRT
<213> ORGANISM: Homo sapiens
<220> FEATURE:
<221> NAME/KEY: PEPTIDE
<222> LOCATION: (1)..(377)
<223> OTHER INFORMATION: Human caspase-4 protein
```

```
<400> SEQUENCE: 1

Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
                20                  25                  30

Asn Val Leu Asn Trp Lys Glu Glu Lys Lys Lys Tyr Tyr Asp Ala
            35                  40                  45

Lys Thr Glu Asp Lys Val Arg Val Met Ala Asp Ser Met Gln Glu Lys
        50                  55                  60

Gln Arg Met Ala Gly Gln Met Leu Leu Gln Thr Phe Phe Asn Ile Asp
65                  70                  75                  80

Gln Ile Ser Pro Asn Lys Lys Ala His Pro Asn Met Glu Ala Gly Pro
                85                  90                  95

Pro Glu Ser Gly Glu Ser Thr Asp Ala Leu Lys Leu Cys Pro His Glu
                100                 105                 110

Glu Phe Leu Arg Leu Cys Lys Glu Arg Ala Glu Glu Ile Tyr Pro Ile
            115                 120                 125

Lys Glu Arg Asn Asn Arg Thr Arg Leu Ala Leu Ile Ile Cys Asn Thr
130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
        195                 200                 205

Ser His Gly Ile Leu Glu Gly Ile Cys Gly Thr Val His Asp Glu Lys
210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Cys Arg Gly Ala Asn Arg Gly Glu Leu Trp Val Arg Asp Ser Pro
                260                 265                 270

Ala Ser Leu Glu Val Ala Ser Ser Gln Ser Ser Glu Asn Leu Glu Glu
            275                 280                 285

Asp Ala Val Tyr Lys Thr His Val Glu Lys Asp Phe Ile Ala Phe Cys
290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
            340                 345                 350

Pro Arg Ala Lys Ala Gln Met Pro Thr Ile Glu Arg Leu Ser Met Thr
        355                 360                 365

Arg Tyr Phe Tyr Leu Phe Pro Gly Asn
        370                 375

<210> SEQ ID NO 2
<211> LENGTH: 1131
<212> TYPE: DNA
```

```
<213> ORGANISM: Artificial Sequence
<220> FEATURE:
<223> OTHER INFORMATION: Polynucleotide encoding human caspase-4 protein

<400> SEQUENCE: 2
atggagggta atcatcggaa aaaaccgctg aaggtgctcg aatcactggg caaagacttt      60
cttactggtg tgctggataa cttggtcgaa caaaacgttc tgaactggaa agaagaagag     120
aaaaaaaaat actatgatgc aaaaaacgaa gacaaggttc gcgtaatggc ggattcaatg     180
caggagaaac aacggatggc tggtcagatg cttctgcaga ccttttttcaa tattgatcag     240
attagcccaa acaagaaagc gcatccgaac atggaggccg gtcctccgga gagcggagaa     300
agtaccgatg ctctgaagtt atgtccacac gaagagtttc tgcgtctttg taaagaacgg     360
gctgaggaga tttatcccat caaagagcgt aataatcgta cacgtctggc gctgattatc     420
tgcaatacag aatttgatca tctgccgccg cgcaatggtg ccgacttcga tatcacgggg     480
atgaaggaac tgctgaagg tttagattac tccgttgacg tagaggaaaa tcttaccgcc     540
cgcgatatgg aaagtgcttt gcgtgcgttc gcaacccggc ccgaacacaa aagttcggat     600
agtactttcc tggtgctcat gtcccacggg attctggaag gcatctgcgg tacggtccat     660
gacgaaaaga aacctgatgt tcttctgtat gacaccatct ttcaaatctt taacaaccgc     720
aactgtttat ccctgaaaga taaacccaag gtgatcattg tccaggcttg tcgggggggca    780
aaccgcggcg agctgtgggt gcgtgactct cctgcaagtc tcgaagttgc ttcaagccaa     840
tcatcggaaa acctggagga agacgcagtc tataaaactc atgttgagaa ggatttttatc    900
gcgttctgct ctagtacacc tcataatgtg tcttggcgcg actcgaccat ggggtcaatc     960
ttcattacgc aactgatcac ctgttttcag aagtacagct ggtgttgcca tctcgaagaa    1020
gttttccgca aagtgcaaca gtcatttgag actccgcgtg ccaaagcgca aatgccgacc    1080
atcgaacgcc tctcgatgac acggtatttc tatcttttc cgggtaattg a              1131

<210> SEQ ID NO 3
<211> LENGTH: 31
<212> TYPE: DNA
<213> ORGANISM: Artificial Sequence
<220> FEATURE:
<223> OTHER INFORMATION: Forward primer for amplifying caspase-4
      polynucleotide

<400> SEQUENCE: 3
aggtcgtcat atggctgagg gtaatcattc g                                     31

<210> SEQ ID NO 4
<211> LENGTH: 39
<212> TYPE: DNA
<213> ORGANISM: Artificial Sequence
<220> FEATURE:
<223> OTHER INFORMATION: Reverse primer for amplifying caspase-4
      polynucleotide

<400> SEQUENCE: 4
ccgcaagctt tcaattaccc ggaaaaagat agaaatacc                             39

<210> SEQ ID NO 5
<211> LENGTH: 29
<212> TYPE: DNA
<213> ORGANISM: Artificial Sequence
<220> FEATURE:
<223> OTHER INFORMATION: Forward primer for amplifying caspase-4(C258A)
      polynucleotide
```

-continued

```
<400> SEQUENCE: 5
tcattgtcca ggctgctcgg ggggcaaac                                    29

<210> SEQ ID NO 6
<211> LENGTH: 29
<212> TYPE: DNA
<213> ORGANISM: Artificial Sequence
<220> FEATURE:
<223> OTHER INFORMATION: Reverse primer for amplifying caspase-4(C258A)
      polynucleotide

<400> SEQUENCE: 6
gtttgccccc cgagcagcct ggacaatga                                    29

<210> SEQ ID NO 7
<211> LENGTH: 377
<212> TYPE: PRT
<213> ORGANISM: Artificial Sequence
<220> FEATURE:
<223> OTHER INFORMATION: Caspase-4(C258A) protein

<400> SEQUENCE: 7
```

Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
            20                  25                  30

Asn Val Leu Asn Trp Lys Glu Glu Lys Lys Lys Tyr Tyr Asp Ala
        35                  40                  45

Lys Thr Glu Asp Lys Val Arg Val Met Ala Asp Ser Met Gln Glu Lys
50                  55                  60

Gln Arg Met Ala Gly Gln Met Leu Leu Gln Thr Phe Phe Asn Ile Asp
65                  70                  75                  80

Gln Ile Ser Pro Asn Lys Lys Ala His Pro Asn Met Glu Ala Gly Pro
                85                  90                  95

Pro Glu Ser Gly Glu Ser Thr Asp Ala Leu Lys Leu Cys Pro His Glu
            100                 105                 110

Glu Phe Leu Arg Leu Cys Lys Glu Arg Ala Glu Glu Ile Tyr Pro Ile
        115                 120                 125

Lys Glu Arg Asn Asn Arg Thr Arg Leu Ala Leu Ile Ile Cys Asn Thr
130                 135                 140

Glu Phe Asp His Leu Pro Pro Arg Asn Gly Ala Asp Phe Asp Ile Thr
145                 150                 155                 160

Gly Met Lys Glu Leu Leu Glu Gly Leu Asp Tyr Ser Val Asp Val Glu
                165                 170                 175

Glu Asn Leu Thr Ala Arg Asp Met Glu Ser Ala Leu Arg Ala Phe Ala
            180                 185                 190

Thr Arg Pro Glu His Lys Ser Ser Asp Ser Thr Phe Leu Val Leu Met
        195                 200                 205

Ser His Gly Ile Leu Glu Gly Ile Cys Gly Thr Val His Asp Glu Lys
210                 215                 220

Lys Pro Asp Val Leu Leu Tyr Asp Thr Ile Phe Gln Ile Phe Asn Asn
225                 230                 235                 240

Arg Asn Cys Leu Ser Leu Lys Asp Lys Pro Lys Val Ile Ile Val Gln
                245                 250                 255

Ala Ala Arg Gly Ala Asn Arg Gly Glu Leu Trp Val Arg Asp Ser Pro
            260                 265                 270

Ala Ser Leu Glu Val Ala Ser Ser Gln Ser Ser Glu Asn Leu Glu Glu

```
            275                 280                 285
Asp Ala Val Tyr Lys Thr His Val Glu Lys Asp Phe Ile Ala Phe Cys
    290                 295                 300

Ser Ser Thr Pro His Asn Val Ser Trp Arg Asp Ser Thr Met Gly Ser
305                 310                 315                 320

Ile Phe Ile Thr Gln Leu Ile Thr Cys Phe Gln Lys Tyr Ser Trp Cys
                325                 330                 335

Cys His Leu Glu Glu Val Phe Arg Lys Val Gln Gln Ser Phe Glu Thr
            340                 345                 350

Pro Arg Ala Lys Ala Gln Met Pro Thr Ile Glu Arg Leu Ser Met Thr
        355                 360                 365

Arg Tyr Phe Tyr Leu Phe Pro Gly Asn
    370                 375

<210> SEQ ID NO 8
<211> LENGTH: 1134
<212> TYPE: DNA
<213> ORGANISM: Artificial Sequence
<220> FEATURE:
<223> OTHER INFORMATION: Polynucleotide encoding caspase-4(C258A)
      protein

<400> SEQUENCE: 8
atggctgagg gtaatcatcg gaaaaaaccg ctgaaggtgc tcgaatcact gggcaaagac      60
tttcttactg gtgtgctgga taacttggtc gaacaaaacg ttctgaactg gaaagaagaa     120
gagaaaaaaa aatactatga tgcaaaaacg gaagacaagg ttcgcgtaat ggcggattca     180
atgcaggaga acaacggat ggctggtcag atgcttctgc agaccttttt caatattgat     240
cagattagcc caaacaagaa agcgcatccg aacatggagg ccggtcctcc ggagagcgga     300
gaaagtaccg atgctctgaa gttatgtcca cacgaagagt ttctgcgtct ttgtaaagaa     360
cgggctgagg agatttatcc catcaaagag cgtaataatc gtacacgtct ggcgctgatt     420
atctgcaata cagaatttga tcatctgccg ccgcgcaatg gtgccgactt cgatatcacg     480
gggatgaagg aactgctgga aggtttagat tactccgttg acgtagagga aaatcttacc     540
gcccgcgata tggaaagtgc tttgcgtgcg ttcgcaaccc ggcccgaaca caaaagttcg     600
gatagtactt tcctggtgct catgtcccac gggattctgg aaggcatctg cggtacggtc     660
catgacgaaa agaaacctga tgttcttctg tatgacacca tctttcaaat ctttaacaac     720
cgcaactgtt atccctgaa agataaaccc aaggtgatca ttgtccaggc tgctcggggg     780
gcaaaccgcg gcgagctgtg ggtgcgtgac tctcctgcaa gtctcgaagt tgcttcaagc     840
caatcatcgg aaaacctgga ggaagacgca gtctataaaa ctcatgttga aaggattttt     900
atcgcgttct gctctagtac acctcataat gtgtcttggc gcgactcgac catgggtca     960 atcttcatta cgcaactgat cacctgtttt cagaagtaca gctggtgttg ccatctcgaa    1020
gaagttttcc gcaaagtgca acagtcattt gagactccgc gtgccaaagc gcaaatgccg    1080
accatcgaac gcctctcgat gacacggtat ttctatcttt ttccgggtaa ttga          1134

<210> SEQ ID NO 9
<211> LENGTH: 80
<212> TYPE: PRT
<213> ORGANISM: Artificial Sequence
<220> FEATURE:
<223> OTHER INFORMATION: Caspase-4 CARD polypeptide

<400> SEQUENCE: 9
```

```
Met Ala Glu Gly Asn His Arg Lys Lys Pro Leu Lys Val Leu Glu Ser
1               5                   10                  15

Leu Gly Lys Asp Phe Leu Thr Gly Val Leu Asp Asn Leu Val Glu Gln
            20                  25                  30

Asn Val Leu Asn Trp Lys Glu Glu Lys Lys Lys Tyr Tyr Asp Ala
        35                  40                  45

Lys Thr Glu Asp Lys Val Arg Val Met Ala Asp Ser Met Gln Glu Lys
    50                  55                  60

Gln Arg Met Ala Gly Gln Met Leu Leu Gln Thr Phe Phe Asn Ile Asp
65                  70                  75                  80

<210> SEQ ID NO 10
<211> LENGTH: 243
<212> TYPE: DNA
<213> ORGANISM: Artificial Sequence
<220> FEATURE:
<223> OTHER INFORMATION: Polynucleotide encoding caspase-4 CARD
      polypeptide

<400> SEQUENCE: 10
atggctgagg gtaatcatcg gaaaaaaccg ctgaaggtgc tcgaatcact gggcaaagac      60
tttcttactg gtgtgctgga taacttggtc gaacaaaacg ttctgaactg gaaagaagaa     120
gagaaaaaaa aatactatga tgcaaaaacg gaagacaagg ttcgcgtaat ggcggattca     180
atgcaggaga acaacggat ggctggtcag atgcttctgc agaccttttt caatattgat     240
tga                                                                   243

<210> SEQ ID NO 11
<211> LENGTH: 45
<212> TYPE: DNA
<213> ORGANISM: Artificial Sequence
<220> FEATURE:
<223> OTHER INFORMATION: Forward primer for amplifying caspase-4 CARD
      polynucleotide

<400> SEQUENCE: 11
tctgcagacc tttttcaata ttgattgaaa gcttgcggcc gcact                     45

<210> SEQ ID NO 12
<211> LENGTH: 45
<212> TYPE: DNA
<213> ORGANISM: Artificial Sequence
<220> FEATURE:
<223> OTHER INFORMATION: Reverse primer for amplifying caspase-4 CARD
      polynucleotide

<400> SEQUENCE: 12
agtgcggccg caagctttca atcaatattg aaaaaggtct gcaga                     45

<210> SEQ ID NO 13
<211> LENGTH: 80
<212> TYPE: PRT
<213> ORGANISM: Artificial Sequence
<220> FEATURE:
<223> OTHER INFORMATION: Caspase-11 CARD polypeptide

<400> SEQUENCE: 13

Met Ala Glu Asn Lys His Pro Asp Lys Pro Leu Lys Val Leu Glu Gln
1               5                   10                  15

Leu Gly Lys Glu Val Leu Thr Glu Tyr Leu Glu Lys Leu Val Gln Ser
            20                  25                  30

Asn Val Leu Lys Leu Lys Glu Glu Asp Lys Gln Lys Phe Asn Asn Ala
```

```
                    35                  40                  45
Glu Arg Ser Asp Lys Arg Trp Val Phe Val Asp Ala Met Lys Lys Lys
    50                  55                  60

His Ser Lys Val Gly Glu Met Leu Leu Gln Thr Phe Phe Ser Val Asp
65                  70                  75                  80

<210> SEQ ID NO 14
<211> LENGTH: 243
<212> TYPE: DNA
<213> ORGANISM: Artificial Sequence
<220> FEATURE:
<223> OTHER INFORMATION: Polynucleotide encoding caspase-11 CARD
      polypeptide

<400> SEQUENCE: 14
atggccgaaa acaagcaccc cgacaaaccc ctgaaagtat tggaacaact gggaaaggaa      60
gttctgacgg agtaccttga aaaattagtc caatccaatg tttttaaagct gaaagaggaa    120 gacaaaacaga agtttaacaa cgctgagcgc tctgacaaac gctgggtttt cgtcgatgcg    180
atgaagaaaa acattcaaa ggtcggcgag atgctgcttc agacttttttt ttccgttgat     240 tga                                                                   243

<210> SEQ ID NO 15
<211> LENGTH: 28
<212> TYPE: DNA
<213> ORGANISM: Artificial Sequence
<220> FEATURE:
<223> OTHER INFORMATION: Forward primer for amplifying caspase-11 CARD
      polynucleotide

<400> SEQUENCE: 15
aggtcgtcat atggccgaaa acaagcac                                         28

<210> SEQ ID NO 16
<211> LENGTH: 39
<212> TYPE: DNA
<213> ORGANISM: Artificial Sequence
<220> FEATURE:
<223> OTHER INFORMATION: Reverse primer for amplifying caspase-11 CARD
      polynucleotide

<400> SEQUENCE: 16
agcgtactcg agtcaatcaa cggaaaaaaa agtctgaag                             39
```